US00PP22673P2

(12) United States Plant Patent
Stemkens

(10) Patent No.: US PP22,673 P2
(45) Date of Patent: Apr. 17, 2012

(54) ***MIMULUS* PLANT NAMED 'MIMAPRI'**

(50) Latin Name: *Mimulus aurantiacus*
Varietal Denomination: Mimapri

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 13 days.

(21) Appl. No.: 12/927,518

(22) Filed: Nov. 17, 2010

(51) Int. Cl.
*A01H 5/00* (2006.01)

(52) U.S. Cl. ..... Plt./454

(58) Field of Classification Search ..... Plt./454
See application file for complete search history.

*Primary Examiner* — Susan McCormick Ewoldt
(74) *Attorney, Agent, or Firm* — S. Matthew Edwards

(57) ABSTRACT

A new *Mimulus* plant named 'Mimapri' particularly distinguished by the large, orange-red flowers, glossy medium green foliage, with upright and tiered plant habit.

1 Drawing Sheet

Latin name of the genus and species of the plant claimed: *Mimulus aurantiacus*.

Varietal denomination: 'Mimapri'.

BACKGROUND OF THE NEW PLANT

The present invention comprises a new *Mimulus*, botanically known as *Mimulus aurantiacus*, and hereinafter referred to by the variety name 'Mimapri'.

'Mimapri' is a product of a planned breeding program. The new cultivar has large, orange-red flowers, glossy medium green foliage, with upright and tiered plant habit.

'Mimapri' originated from a hybridization made in July 2001 in a controlled breeding environment in Gilroy, Calif. The female parent was an unpatented, proprietary plant designated 'CO126-1' with yellow flowers, a more trailing habit and less branching.

The male parent of 'Mimapri' was an unpatented, proprietary plant identified as 'CO134-1' with pink flowers, larger flower size and lighter green foliage. The resultant seed was sown in February 2002.

'Mimapri' was selected as one flowering plant within the progeny of the stated cross in August 2002 in a controlled environment in Gilroy, Calif.

The first act of asexual reproduction of 'Mimapri' was accomplished when vegetative cuttings were propagated from the initial selection in August 2002 in a controlled environment in Gilroy, Calif.

BRIEF SUMMARY OF INVENTION

Horticultural examination of plants grown from cuttings of the plant initiated in August 2002, and continuing thereafter, has demonstrated that the combination of characteristics as herein disclosed for 'Mimapri' are firmly fixed and are retained through successive generations of asexual reproduction.

'Mimapri' has not been observed under all possible environmental conditions. The phenotype may vary significantly with variations in environment such as temperature, light intensity and day length.

A Plant Breeder's Right for this cultivar has been applied for in Canada on Feb. 9, 2010 (No. 10-6824). 'Mimapri' has not been made publicly available more than one year prior to the filing of this application.

The following traits have been repeatedly observed and are determined to be basic characteristics of the new variety. The combination of these characteristics distinguishes this *Mimulus* as a new and distinct variety.

BRIEF DESCRIPTION OF THE PHOTOGRAPHS

The accompanying photographic drawing shows typical flower and foliage characteristics of 'Mimapri' with colors being as true as possible with an illustration of this type. The photographic drawing shows a flowering plant of the new variety and a close-up of the flowers. These photographs were taken in September 2009 of plants growing in a field trial in Gilroy, Calif.

DETAILED BOTANICAL DESCRIPTION

The plant descriptions and measurements were taken in late August 2010 under natural light. These plants were growing in field trials in Gilroy, Calif. These plants were about 20-22 weeks of age.

Color references are made to The Royal Horticultural Society Colour Chart (R.H.S.) 2001.

TABLE 1

DIFFERENCES BETWEEN THE NEW VARIETY 'MIMAPRI' AND A SIMILAR VARIETY: 'JELLY BEAN APRICOT' (U.S. Plant Pat. No. 11,970)

| | 'Mimapri' | 'Jelly Bean Apricot' |
|---|---|---|
| Flower color in general: | Orange-apricot | More pink-apricot |
| Flowering response: | Earlier | Later |
| Plant habit: | More upright | More trailing |

Plant:

*Form, growth and habit.*—Upright, somewhat tiered and slightly open habit; removal of terminal apices (pinching) enhances branching habit.

*Plant height*.—About 34-40 cm.
*Plant height* (*inflorescence included*).—About 45.0 cm.
*Plant width*.—40-50 cm.
*Garden performance and tolerance to weather*.—Very good.

Roots:
*Number of days to initiate and develop roots*.—18-20 days at about 22 degrees C.
*Type*.—Fine, fibrous, free branching.
*Color*.—RHS N155B but whiter.

Foliage:
*Arrangement*.—Alternate, simple.
*Immature, leaf color, upper surface*.—RHS 137A but a little darker.
*Lower surface*.—RHS 146B.
*Mature, leaf color, upper surface*.—RHS 137A but a little darker.
*Lower surface*.—RHS 146B.
*Length*.—4.5-5.2 cm.
*Width*.—1.1-1.3 cm.
*Shape*.—Lanceolate.
*Base shape*.—Cuncate.
*Apex shape*.—Acute to obtuse.
*Margin*.—Entire to slightly serrulate.
*Texture, upper surface*.—Glossy with glandular hairs.
*Lower surface*.—Glandular hairs.
*Color of veins, upper surface*.—Basally RHS 144B otherwise indistinct.
*Color of veins, lower surface*.—Basally RHS 144B otherwise indistinct.

Stem:
*Quantity of main stems per plant*.—4-5.
*Color of stem*.—RHS 144A overlaid with anthocyanins of between RHS 166B and RHS 172B.
*Length of stem*.—45 cm.
*Diameter*.—0.3-0.4 cm.
*Length of internodes*.—0.4-0.5 cm.
*Texture*.—Glandular hairs; hispid.
*Color of pedicels*.—RHS 144B but sometimes with slight anthocyanin specks of about RHS N170B.
*Length of pedicels*.—0.5-0.7 cm.
*Diameter of pedicels*.—0.1-0.15 cm.
*Texture*.—Glandular hairs.

Inflorescence:
*Type*.—On first flowering it appears to be a raceme, then matures to more of a panicle or thyrse; flowers are held somewhat horizontally to slightly upwards with single, axillary, salverform and zygomorphic flowers.
*Quantity of inflorescences per plant*.—About 100.
*Lastingness of individual blooms on the plant*.—12-14 days outside.
*Fragrance*.—None.

Bud (just when opening/showing color):
*Color*.—RHS 179A basally with RHS 179B apex suffused with RHS 170B.
*Length*.—3.5-3.7 cm.
*Width*.—1.0 cm.
*Shape*.—Oblong.

Immature inflorescence:
*Diameter*.—3.2 cm.
*Color, upper surface*.—Between RHS 25A and RHS 25B ground color; heavily overlaid with RHS N25A, with RHS 34A striations and RHS 25B margins.
*Lower surface*.—RHS 25A, overlaid with RHS N25A.

Mature inflorescence:
*Hortizontal diameter*.—About 4.3 cm.
*Vertical height*.—5.0-5.2 cm.
*Depth*.—5.0-6.0 cm.

Corolla:
*Color upper lobes, upper surface*.—Between RHS 25A and RHS 25B with a light suffusion of RHS N25A and with slight blotches of RHS 34B at the corolla opening.
*Color upper lobes, lower surface*.—RHS 25C with a light overlay of RHS 25B.
*Length of upper lobes*.—2.2 cm.
*Width of upper lobes*.—1.5 cm.
*Color lateral lobes, upper surface*.—Between RHS 25A and RHS 25B with a light suffusion of RHS N25A and with slight blotches of RHS 34B at the corolla opening.
*Color lateral lobes, lower surface*.—RHS 25C with a light overlay of RHS 25B.
*Length of lateral lobes*.—1.4 cm.
*Width of lateral lobes*.—1.1 cm.
*Color lower mid-lobe, upper surface*.—Between RHS 25A and RHS 25B with a light suffusion of RHS N25A and with slight blotches of RHS 34B at the corolla opening.
*Color lower mid-lobe, lower surface*.—RHS 25C with a light overlay of RHS25B.
*Length of lower mid-lobe*.—1.6 cm.
*Width of lower mid-lobe*.—1.0 cm.
*Apex shape, upper lobe*.—Obtuse.
*Apex shape, lower lobes*.—Widely emarginate.
*Margin* (*all lobes*).—Entire.
*Petal texture, upper surface* (*all lobes*).—Papillose.
*Lower surface* (*all lobes*).—Papilose, some glandular hairs, some hispid.
*Corolla tube color, inside*.—RHS N155B.
*Corolla tube color, outside*.—Between RHS N25B and RHS N25C heavily overlaid with RHS N34C to RHS 34D blotches.
*Corolla tube length*.—About 3.5 cm.

Sepals:
*Quantity*.—5, mostly fused at the margins with slight free apices.
*Color, upper surface*.—RHS 144B basally with RHS 144A apex.
*Lower surface*.—RHS 144B basally with RHS 144A apex.
*Length*.—2.4-2.7 cm.
*Width*.—Not observed due to fusion.
*Shape*.—Oblong.
*Apex shape*.—Acute.
*Based*.—Fused.
*Margins*.—Entire.
*Texture, upper surface*.—Glandular hairs.
*Lower surface*.—Glandular hairs.

Reproductive organs:
*Pistil*.—1.
*Length*.—4.2 cm.
*Style color*.—RHS 155B.
*Style length*.—3.3 cm.
*Stigma color*.—RHS 155B.
*Stigma shape*.—Bi-parted.
*Ovary color*.—RHS 145B.
*Ovary length*.—0.4-0.5 cm.
*Ovary diameter*.—0.15-0.2 cm.

*Stamens*.—Quantity: 4.
*Color of filaments*.—RHS 16B basally with RHS 16A apex.
*Length filaments*.—3.0-3.4 cm.
*Anther color*.—RHS 7A.
*Anther length*.—0.2-0.3 cm.
*Anther shape*.—Ovoid; bi-lobed.
*Color of pollen*.—RHS 15A.
*Pollen amount*.—Moderate.
*Fertility/seed set*.—Has not been observed on this hybrid.

Disease/pest resistance: Disease/pest resistance has not been observed on this hybrid.

What is claimed is:

1. A new and distinct variety of *Mimulus* plant named 'Mimapri' substantially as illustrated and described herein.

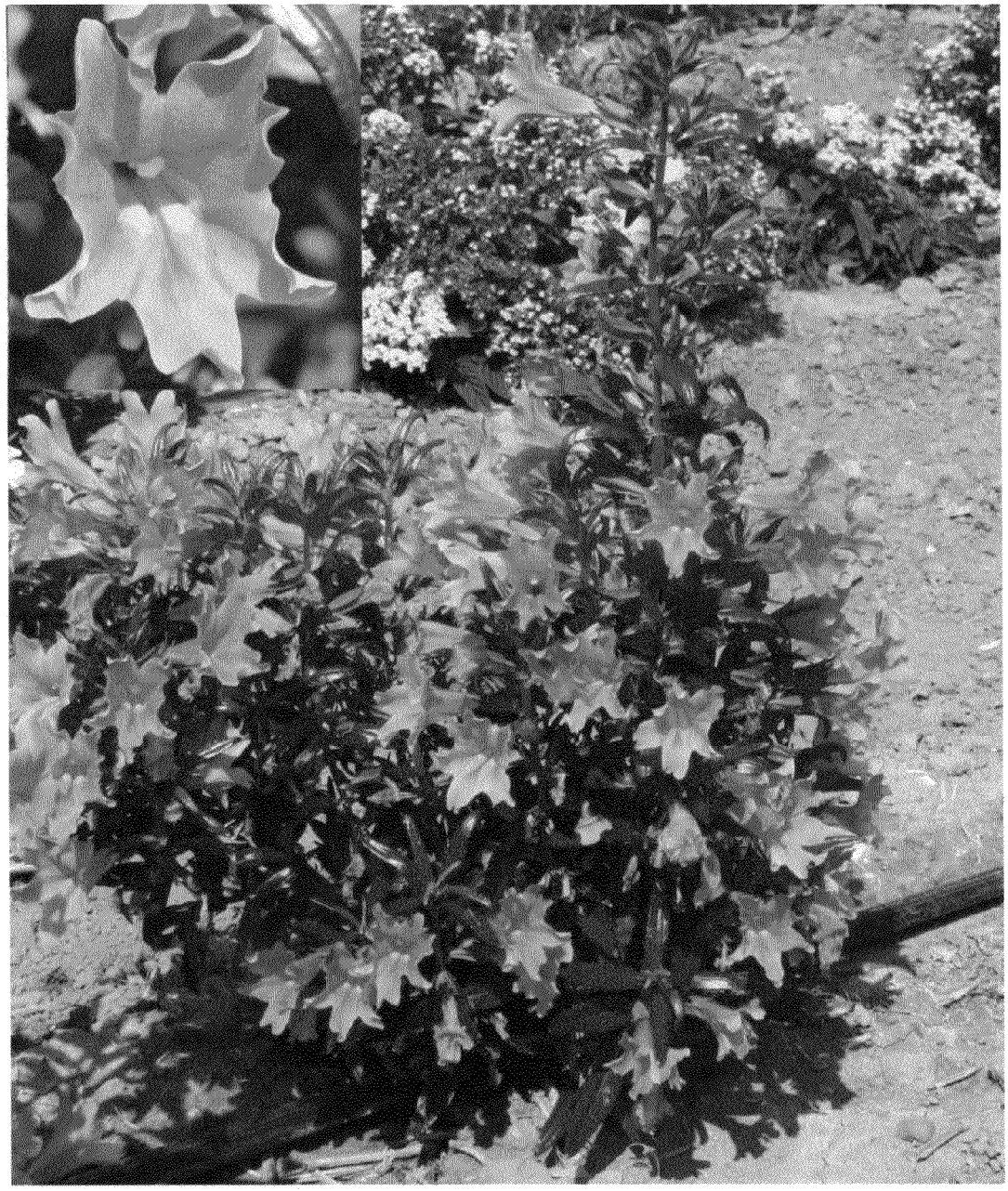

* * * * *